(12) United States Patent
Zhu et al.

(10) Patent No.: US 9,822,488 B2
(45) Date of Patent: Nov. 21, 2017

(54) ULTRALONG HYDROXYAPATITE NANOWIRE/MICROWIRE, METHOD OF PREPARING SAME, HYDROXYAPATITE PAPER COMPRISING SAME AND PREPARATION METHOD THEREOF

(71) Applicant: SHANGHAI INSTITUTE OF CERAMICS, CHINESE ACADEMY OF SCIENCES, Shanghai (CN)

(72) Inventors: Yingjie Zhu, Shanghai (CN); Bingqiang Lu, Shanghai (CN); Feng Chen, Shanghai (CN)

(73) Assignee: Shanghai Institute of Ceramics, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/102,494

(22) PCT Filed: Sep. 29, 2014

(86) PCT No.: PCT/CN2014/087742
§ 371 (c)(1),
(2) Date: Jun. 7, 2016

(87) PCT Pub. No.: WO2015/085814
PCT Pub. Date: Jun. 18, 2015

(65) Prior Publication Data
US 2017/0022668 A1 Jan. 26, 2017

(30) Foreign Application Priority Data
Dec. 13, 2013 (CN) .......................... 2013 1 0687363

(51) Int. Cl.
| | |
|---|---|
| *D21H 13/46* | (2006.01) |
| *C01B 25/32* | (2006.01) |
| *A61L 27/12* | (2006.01) |
| *C04B 35/447* | (2006.01) |
| *C04B 35/622* | (2006.01) |
| *D01F 9/08* | (2006.01) |
| *D21H 21/52* | (2006.01) |
| *A61L 27/42* | (2006.01) |
| *C04B 35/63* | (2006.01) |
| *C04B 35/634* | (2006.01) |
| *D21H 17/68* | (2006.01) |
| *B82Y 30/00* | (2011.01) |
| *B82Y 40/00* | (2011.01) |

(52) U.S. Cl.
CPC .............. *D21H 13/46* (2013.01); *A61L 27/12* (2013.01); *A61L 27/425* (2013.01); *C01B 25/322* (2013.01); *C04B 35/447* (2013.01); *C04B 35/62268* (2013.01); *C04B 35/6303* (2013.01); *C04B 35/634* (2013.01); *C04B 35/6316* (2013.01); *D01F 9/08* (2013.01); *D21H 17/68* (2013.01); *D21H 21/52* (2013.01); *A61L 2400/12* (2013.01); *B82Y 30/00* (2013.01); *B82Y 40/00* (2013.01); *C04B 2235/34* (2013.01); *C04B 2235/443* (2013.01); *C04B 2235/444* (2013.01); *C04B 2235/447* (2013.01); *C04B 2235/449* (2013.01); *C04B 2235/526* (2013.01); *C04B 2235/5264* (2013.01)

(58) Field of Classification Search
CPC ........... D21H 13/46; D21H 17/68; D21F 9/08
USPC ........................................................ 162/152
See application file for complete search history.

(56) References Cited

FOREIGN PATENT DOCUMENTS

| | | |
|---|---|---|
| CN | 2908593 Y | 6/2007 |
| CN | 101297978 A | 11/2008 |
| CN | 101723341 A | 6/2010 |
| CN | 103407979 A | 11/2013 |
| CN | 103626144 A | 3/2014 |
| CN | 103850152 A | 6/2014 |

OTHER PUBLICATIONS

CN 103850152, machine translation Jun. 2014.*
CN 103626144, machine translation, Mar. 2014.*
CN 2908593, machine translation, Jun. 2007.*
CN 103407979, machine translation, Nov. 2013.*

* cited by examiner

*Primary Examiner* — Mark Halpern
(74) *Attorney, Agent, or Firm* — Brian E. Davy; Bozicevic, Field & Francis LLP

(57) ABSTRACT

The invention relates to an ultralong hydroxyapatite nanowire/microwire, a method of preparing the same, a hydroxyapatite paper comprising the same and a preparation method thereof, and provides an ultralong hydroxyapatite nanowire/microwire having a length of tens to hundreds of micrometers and a diameter of tens to hundreds of nanometers. There is also provided a method of preparing the ultralong hydroxyapatite nanowire/microwire, a hydroxyapatite paper comprising the ultralong hydroxyapatite nanowire/microwire, and a method of preparing the hydroxyapatite paper.

5 Claims, 4 Drawing Sheets

US 9,822,488 B2

ULTRALONG HYDROXYAPATITE NANOWIRE/MICROWIRE, METHOD OF PREPARING SAME, HYDROXYAPATITE PAPER COMPRISING SAME AND PREPARATION METHOD THEREOF

This application is a 371 of PCT/CN2014/087742 filed 29 Sep. 2014.

TECHNICAL FIELD

The invention pertains to the field of preparing inorganic materials, and relates to a highly flexible, high temperature resistant and nonflammable hydroxyapatite paper and a method of preparing the same. More particularly, the invention relates to an ultralong hydroxyapatite nanowire/microwire, a method of preparing the same, a hydroxyapatite paper comprising the same and a preparation method thereof.

BACKGROUND ART

Paper is a basic material for writing, presswork and printing, and its use has a history over a thousand years. Traditional paper is prepared from plant cellulose and additional auxiliaries by special process. In order to improve paper properties such as whiteness, smooth finish, strength, resolution and the like, a variety of additives such as calcium carbonate, clay, bleaching agent and the like are added as auxiliaries or coatings. Due to development of modern technology and growth of human need, the amount of paper consumed by human beings per year is enormous and increases year by year, leading to increasingly serious problems of disafforestation, environmental pollution, etc. In addition, as lignin in paper yellows under the effect of light and oxygen, paper itself turns yellow along with time, and the quality of writing, presswork and printing is affected badly. Another fatal deficiency of traditional paper is its flammability, which means that books and paper files may burn to nothing in fire. This is one of the main reasons for damage and vanishing of so many paper cultural relics in centuries.

Development of new paper has been started in hopes of solving the environmental problems brought about by traditional paper-making process and improving the utility of the paper. However, it's hard for the utility to achieve the level of traditional paper, and likely pollution to environment occurs in production, application and degradation. In recent years, interest is focused on preparation of paper from inorganic materials as the main components. Nonetheless, such paper preparation is demanding in terms of the inorganic materials which should feature white color, non-toxicity, high flexibility and good processibility into a thin laminate, inter alias. Unfortunately, few inorganic materials can meet these requirements.

As an important calcium phosphate material, hydroxyapatite is the main inorganic ingredient of vertebrate hard tissues, and exhibits the advantages of good biocompatibility, non-toxicity, high whiteness, high temperature resistance, nonflammability, etc. Moreover, hydroxyapatite also exists in sea water in a large quantity. Hence, it owns wide sources and is expected to become an ideal raw material for preparing inorganic paper. However, the use of a hydroxyapatite material is restricted by its poor flexibility. The preparation of a highly flexible hydroxyapatite material is always a big challenge.

Up to now, there is no method in the art for preparing a new hydroxyapatite material having white color, non-toxicity, high temperature resistance, nonflammability, highly flexibility, and good processibility into a thin laminate, which hydroxyapatite material can be used to prepare highly flexible, high temperature resistant and nonflammable hydroxyapatite paper.

SUMMARY

The invention provides a new ultralong hydroxyapatite nanowire/microwire, a method of preparing the same, a hydroxyapatite paper comprising the same and a preparation method thereof, and thus the problems existing in the prior art are solved.

In one aspect, the invention provides an ultralong hydroxyapatite nanowire/microwire having a length of tens to hundreds of micrometers and a diameter of tens to hundreds of nanometers.

In another aspect, the invention provides a method of preparing the above ultralong hydroxyapatite nanowire/microwire, comprising the following steps:

(1) mixing oleic acid and an alcohol, and adding an aqueous solution of a water-soluble calcium salt and an alkali aqueous solution under agitation to form a calcium oleate precursor, wherein the ratio of oleic acid and the alcohol by mass is 1:10 to 10:1;

(2) adding an aqueous solution of a water-soluble phosphorus source to obtain a reaction system, wherein the molar ratio of the water-soluble calcium salt to the water-soluble phosphorus source is 1:10 to 10:1;

(3) solvothermally treating the resulting reaction system at 100-280° C. for 1 hour to 7 days; and (4) separating the resultant product, followed by washing to obtain the ultralong hydroxyapatite nanowire/microwire.

In one preferred embodiment, the washing in step (4) is performed with ethanol and water.

In another preferred embodiment, the alcohol includes but is not limited to ethanol, methanol, propanol, isopropanol, butanol, ethylene glycol and glycerol; the water-soluble calcium salt includes but is not limited to calcium chloride and its hydrates, calcium sulfate and its hydrates, calcium acetate and its hydrates, calcium nitrate and its hydrates; the aqueous solution of the water-soluble calcium salt has a molar concentration of 0.01-10 mol/L; the alkali includes but is not limited to sodium hydroxide, potassium hydroxide, calcium hydroxide, ethylene diamine, ethanolamine, urea and ammonia; and the alkali aqueous solution has a molar concentration of 0.01-10 mol/L.

In another preferred embodiment, the water-soluble phosphorus source includes but is not limited to sodium phosphate, dibasic sodium phosphate, monobasic sodium phosphate, phosphoric acid, potassium phosphate, dibasic potassium phosphate, monobasic potassium phosphate, ammonium phosphate, dibasic ammonium phosphate, monobasic ammonium phosphate, and hydrates thereof; and the aqueous solution of the water-soluble phosphorus source has a molar concentration of 0.01-10 mol/L.

In still another aspect, the invention provides a hydroxyapatite paper comprising the above ultralong hydroxyapatite nanowire/microwire.

In yet another aspect, the invention provides a method of preparing the above hydroxyapatite paper, comprising the following step:

dispersing the above ultralong hydroxyapatite nanowire/microwire in a solvent and adding additives, followed by forming, separation, drying and pressing to obtain the hydroxyapatite paper.

In one preferred embodiment, the solvent is water or an alcohol which includes ethanol, methanol, propanol, isopropanol and butanol.

In another preferred embodiment, the method further comprises adding additives to the solvent, wherein the additives include inorganic additives and organic additives, wherein the inorganic additives include but are not limited to sodium silicate, potassium silicate, sodium borate and potassium borate; and the organic additives include but are not limited to polylactic acid, polyethylene glycol, polyvinyl alcohol, polystyrene and polyurethane.

In another preferred embodiment, the separation includes filtration and vacuum filtration, and the temperature for drying is 20-200° C.

DESCRIPTION OF DRAWINGS

According to the following detailed description with reference to the drawings, the objects and features of the invention will be more apparent, wherein.

DETAILED DESCRIPTION OF THE INVENTION

Figure 1:
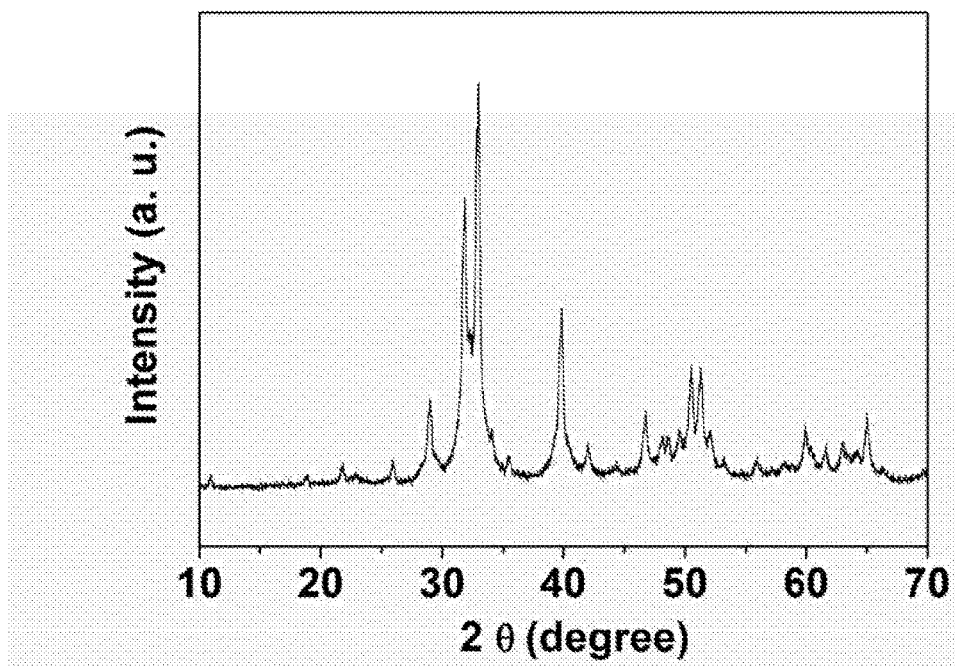
FIG. 1 shows an X-ray diffraction pattern of ultralong hydroxyapatite nanowires according to the invention.
Figure 2:
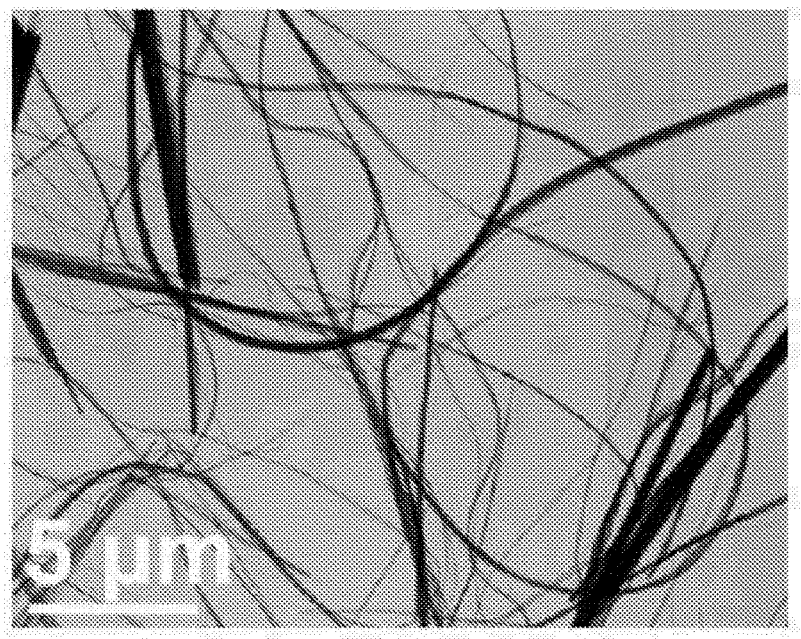
FIG. 2 shows a TEM image of ultralong hydroxyapatite nanowires according to the invention.
Figure 3:
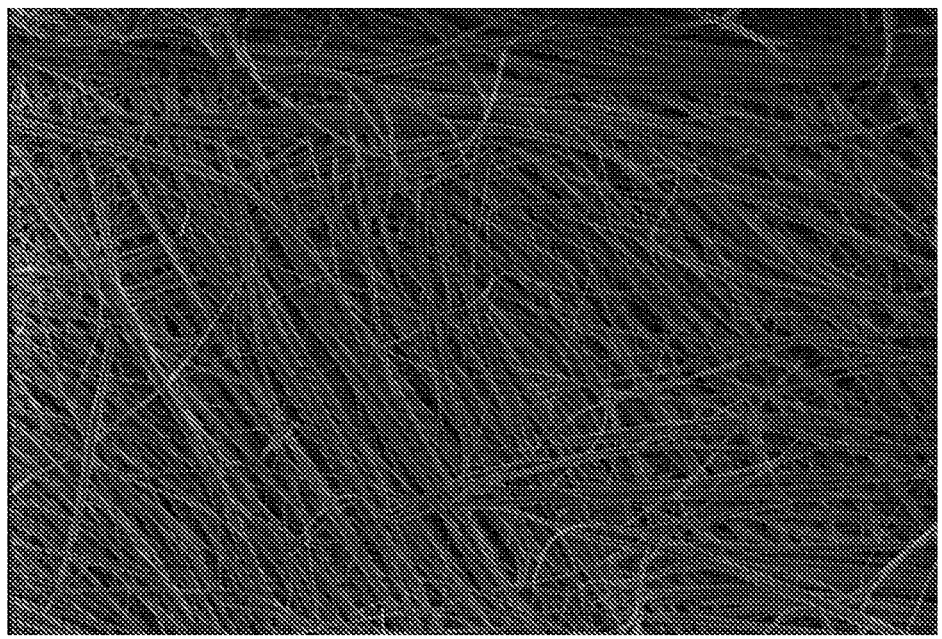
FIG. 3 shows an SEM image of ultralong hydroxyapatite nanowires according to the invention.

Upon extensive and intensive research, the inventors of the application have found that a highly flexible, high temperature resistant, nonflammable hydroxyapatite paper can be prepared from ultralong hydroxyapatite nanowires/microwires prepared according to the invention by dispersing them in a solvent and adding additives, followed by forming, separation, drying and pressing; and, since hydroxyapatite is an inorganic material having high thermal stability and nonflammability, the hydroxyapatite paper prepared therefrom can be used for storing important files and archives for a long time, and this hydroxyapatite paper can also be used in various biomedical areas, pollutant treatment and other fields. The present invention has thus been accomplished on the basis of the foregoing findings.

Ultralong Hydroxyapatite Nanowire/Microwire

In a first aspect of the invention, there is provided a highly flexible ultralong hydroxyapatite nanowire/microwire having a length of tens to hundreds of micrometers and a diameter of tens to hundreds of nanometers.

Preparation of Ultralong Hydroxyapatite Nanowire/Microwire

In a second aspect of the invention, there is provided a method of preparing the ultralong hydroxyapatite nanowire/microwire, comprising the following steps:

(1) mixing oleic acid and an alcohol, and adding an aqueous solution of a water-soluble calcium salt and an alkali aqueous solution under agitation to form a calcium oleate precursor;

(2) adding an aqueous solution of a water-soluble phosphorus source, and transferring the mixture into a reactor to allow for solvothermal reaction to produce an ultralong hydroxyapatite nanowire/microwire product; and (3) separating the resultant product, followed by washing to obtain the ultralong hydroxyapatite nanowire/microwire.

In the invention, the alcohol includes but is not limited to ethanol, methanol, propanol, isopropanol, butanol, ethylene glycol and glycerol; the water-soluble calcium salt includes but is not limited to calcium chloride and its hydrates, calcium sulfate and its hydrates, calcium acetate and its hydrates, calcium nitrate and its hydrates; the alkali includes but is not limited to sodium hydroxide, potassium hydroxide, calcium hydroxide, ethylene diamine, ethanolamine, urea and ammonia.

In the invention, the ratio of oleic acid and the alcohol by mass is 1:10 to 10:1, preferably 1:1.

In the invention, the aqueous solution of the water-soluble calcium salt has a molar concentration of 0.01-10 mol/L, preferably 0.05-5 mol/L; and the alkali aqueous solution has a molar concentration of 0.01-10 mol/L, preferably 0.1-5 mol/L.

In the invention, the water-soluble phosphorus source includes but is not limited to phosphoric acid, sodium phosphate, dibasic sodium phosphate, monobasic sodium phosphate, potassium phosphate, dibasic potassium phosphate, monobasic potassium phosphate, ammonium phosphate, dibasic ammonium phosphate, monobasic ammonium phosphate, and hydrates thereof.

In the invention, the aqueous solution of the water-soluble phosphorus source has a molar concentration of 0.01-10 mol/L, preferably 0.05-5 mol/L.

In the invention, the molar ratio of the water-soluble calcium salt to the water-soluble phosphorus source is 1:10 to 10:1, preferably 1:2-2:1.

In the invention, the solvothermal reaction is conducted at 100-280° C. for 1 hour to 7 days, preferably at 150-200° C. for 5-60 hours.

In the invention, the washing is performed with ethanol and water for several times to obtain the ultralong hydroxyapatite nanowire/microwire.

In the invention, the ultralong hydroxyapatite nanowire/microwire can also be prepared by other methods than the above solvothermal method.

Hydroxyapatite Paper

In a third aspect of the invention, there is provided a hydroxyapatite paper comprising the above ultralong hydroxyapatite nanowire/microwire.

Preparation of Hydroxyapatite Paper

In a fourth aspect of the invention, there is provided a method of preparing the above hydroxyapatite paper, comprising the following step:

dispersing the above ultralong hydroxyapatite nanowire/microwire (preferably nanowire) in a solvent and adding additives, followed by forming, separation, drying and pressing to obtain a highly flexible, high temperature resistant, nonflammable hydroxyapatite paper.

In the invention, the solvent is water or an alcohol which includes but is not limited to ethanol, methanol, propanol, isopropanol and butanol.

In the invention, if necessary, additives may be added to the solvent, wherein the additives include inorganic additives and organic additives, wherein the inorganic additives include but are not limited to sodium silicate, potassium silicate, sodium borate and potassium borate; and the organic additives include but are not limited to polylactic acid, polyethylene glycol, polyvinyl alcohol, polystyrene and polyurethane.

In the invention, the separation includes but is not limited to filtration and vacuum filtration, wherein a Buchner funnel, a common funnel or a glass funnel may be used in the filtration and vacuum filtration. It should be noted that the method of removing the solvent is not limited to filtration and vacuum filtration. Evaporation of the solvent, centrifugation, pressing or other operations may also be used. A combination of two or more operations is also possible. For example, a dispersion liquid of the hydroxyapatite nanowire/microwire may be poured into a vessel to evaporate the solvent and allow for formation of a hydroxyapatite paper from the hydroxyapatite nanowire/microwire at the bottom.

In the invention, the temperature for drying is 20-200° C.

In the invention, the surface nature of the prepared hydroxyapatite paper may be regulated to obtain hydrophobicity or hydrophilicity. The hydroxyapatite paper shows such high flexibility that it can be rolled up without observable damage. It is high temperature resistant and nonflammable. When it is used for printing words, patterns and images in color, the printing quality is very good.

The invention has the following main advantages:

Using the ultralong hydroxyapatite nanowire/microwire prepared by the method of the invention as a raw material, a highly flexible, high temperature resistant, nonflammable hydroxyapatite paper can be obtained by simple forming, separation, drying and pressing treatment, wherein the preparation is featured by simple process, convenient operation, environmental friendliness, exemption from complicated and expensive devices, and adaptability to industrial production. The hydroxyapatite paper prepared exhibits a high level of whiteness, and also such high flexibility that it can be rolled up without observable damage. When it is used for printing words, patterns and images in color, the printing quality is very good. Furthermore, the hydroxyapatite paper prepared is high temperature resistant and nonflammable, and thus can be used for storing important files and archives for a long period of time. It can also be used in various biomedical areas, pollutant treatment and many other fields.

EXAMPLES

The invention will be further illustrated with reference to the following specific examples. However, it should be noted that these examples are only intended to demonstrate the invention without limiting the scope of the invention. In the following examples, the test methods where no specific conditions are indicated are generally carried out under conventional conditions.

Example 1

6.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.13 mol/L aqueous solution of monobasic sodium phosphate dihydrate was added. Then, the mixture was transferred into a reactor, heated to 180° C. and maintained at this temperature for solvothermal treatment for 23 hours. The reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel, vacuum filtered, dried at 60° C. and pressed to obtain a hydroxyapatite paper.

Example 2

6.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.39 mol/L aqueous solution of monobasic sodium phosphate dihydrate was added. Then, the mixture was transferred into a reactor, heated to 180° C. and maintained at this temperature for solvothermal treatment for 23 hours. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel, vacuum filtered, dried at 60° C. and pressed to obtain a hydroxyapatite paper.

Example 3

6.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.13 mol/L aqueous solution of monobasic sodium phosphate dihydrate was added. Then, the mixture was transferred into a reactor, heated to 200° C. and maintained at this temperature for solvothermal treatment for 23 hours. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel, vacuum filtered, dried at 60° C. and pressed to obtain a hydroxyapatite paper.

Example 4

6.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.13 mol/L aqueous solution of monobasic sodium phosphate dihydrate was added. Then, the mixture was transferred into a reactor, heated to 180° C. and maintained at this temperature for solvothermal treatment for 23 hours. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, and 2.000 g $Na_2SiO_3$ was added, then the resulting suspension was poured into a Buchner funnel, vacuum filtered, dried at 60° C. and pressed to obtain a hydroxyapatite paper.

Example 5

3.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.26 mol/L aqueous solution of monobasic sodium phosphate dihydrate was added. Then, the mixture was transferred into a reactor, heated to 180° C. and maintained at this temperature for solvothermal treatment for 23 hours. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel, vacuum filtered, dried at 60° C. and pressed to obtain a hydroxyapatite paper.

Example 6

6.000 g oleic acid and 6.000 g ethanol were mixed, and then 10 mL 0.20 mol/L aqueous solution of calcium chloride and 10 mL 1.25 mol/L aqueous solution of sodium hydroxide were added under agitation to form a precursor. Subsequently, 5 mL 0.26 mol/L aqueous solution of monobasic sodium phosphate dihydrate was added. Then, the mixture was transferred into a reactor, heated to 180° C. and maintained at this temperature for solvothermal treatment for 2 days. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel, vacuum filtered, dried at 60° C. and pressed to obtain a hydroxyapatite paper.

Example 7

6.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.13 mol/L aqueous solution of monobasic sodium phosphate dihydrate was added. Then, the mixture was transferred into a reactor, heated to 180° C. and maintained at this temperature for solvothermal treatment for 6 days. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel and vacuum filtered, dried at 60° C. and pressed to obtain a hydroxyapatite paper.

Example 8

6.000 g oleic acid and 6.000 g ethanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.13 mol/L aqueous solution of dibasic potassium phosphate was added. Then, the mixture was transferred into a reactor, heated to 180° C. and maintained at this temperature for solvothermal treatment for 2 days. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel and vacuum filtered. The product was dried at 60° C. and pressed to obtain a hydroxyapatite paper.

Example 9

6.000 g oleic acid and 6.000 g ethanol were mixed, and then 10 mL 0.10 mol/L aqueous solution of calcium nitrate tetrahydrate and 10 mL 1.25 mol/L aqueous solution of potassium hydroxide were added under agitation to form a precursor. Subsequently, 5 mL 0.13 mol/L aqueous solution of monobasic ammonium phosphate was added. Then, the mixture was transferred into a reactor, heated to 180° C. and maintained at this temperature for solvothermal treatment for 2 days. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel and vacuum filtered. The product was dried at 60° C. and pressed to obtain a hydroxyapatite paper.

Example 10

6.000 g oleic acid and 6.000 g methanol were mixed, and then 10 mL 0.10 mol/L aqueous solution of calcium chloride and 10 mL 1.25 mol/L aqueous solution of sodium hydroxide were added under agitation to form a precursor. Subsequently, 5 mL 0.13 mol/L aqueous solution of monobasic sodium phosphate dihydrate was added. Then, the mixture was transferred into a reactor, heated to 180° C. and maintained at this temperature for solvothermal treatment for 23 hours. The solvothermal reaction product was separated by centrifuge, and washed with ethanol and water several times to obtain the hydroxyapatite nanowire/microwire. The hydroxyapatite nanowire/microwire obtained was dispersed in 100 mL ethanol, poured into a Buchner funnel and vacuum filtered. The product was dried at 60° C. and pressed to obtain a hydroxyapatite paper.

Technical Effects

Figure 4:
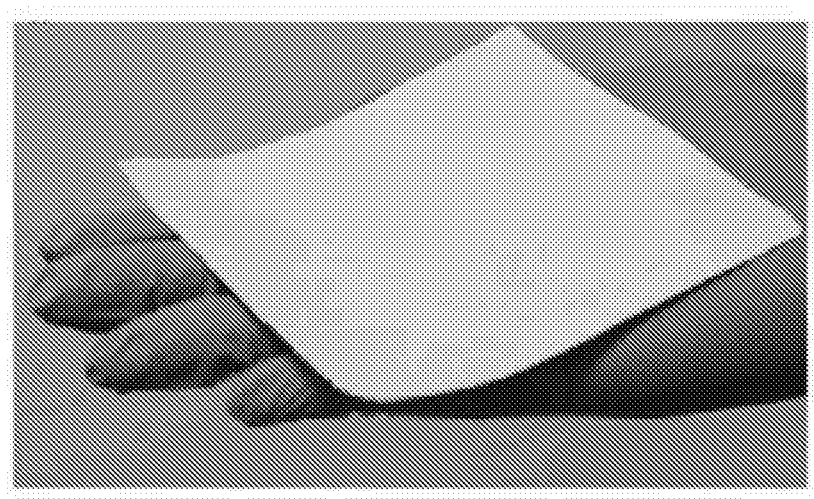
FIG. 4 shows a photo of a highly flexible, high temperature resistant, nonflammable hydroxyapatite paper according to the invention.
Figure 5:
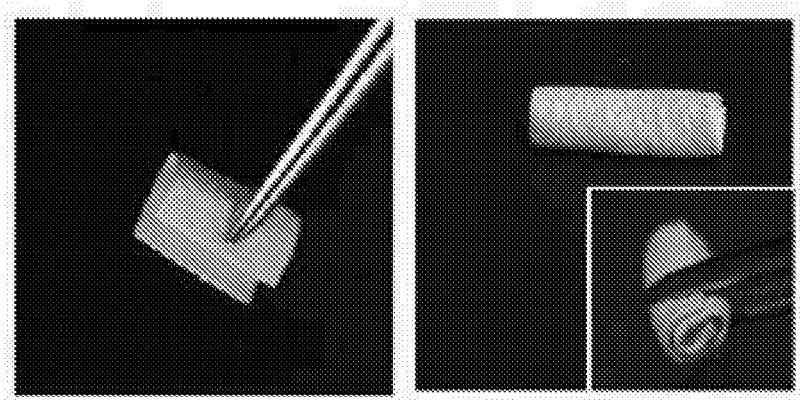
FIG. 5 shows photos exhibiting the flexibility of a highly flexible, high temperature resistant, nonflammable hydroxyapatite paper according to the invention.
Figure 6:
FIG. 6 shows a photo exhibiting the effect of a highly flexible, high temperature resistant, nonflammable hydroxyapatite paper in printing words and patterns according to the invention.
Figure 7:
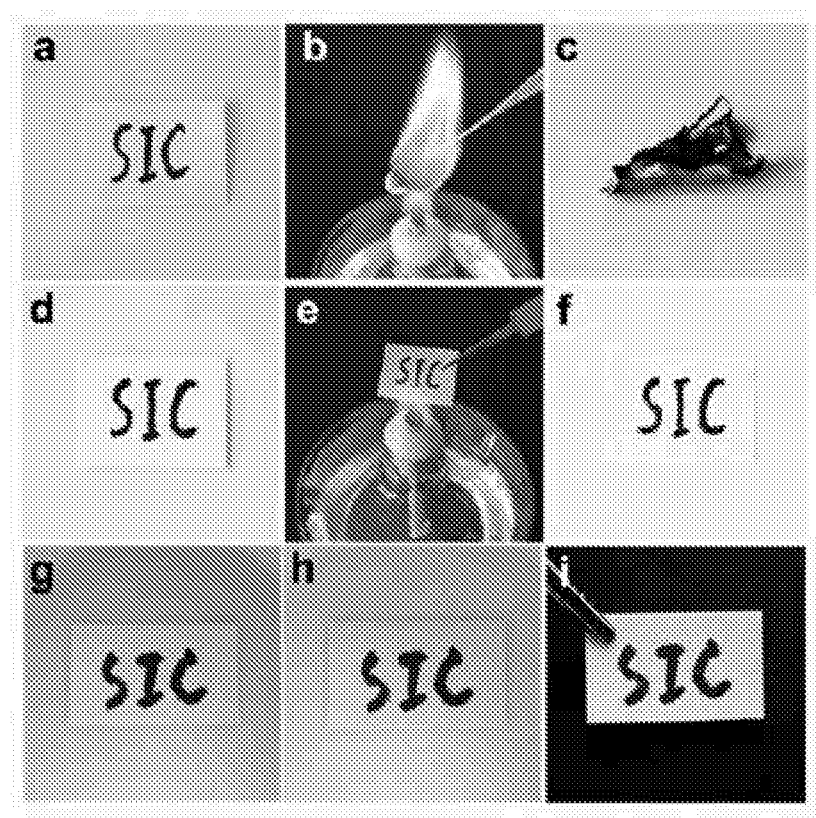
FIG. 7 shows photos exhibiting the thermal stability of a common printing paper and a highly flexible, high temperature resistant, nonflammable hydroxyapatite paper according to the invention, wherein (a-c) are photos of the common printing paper before (a), during (b) and after (c) heating in the flame of an alcohol burner; (d-f) are photos of the prepared highly flexible, high temperature resistant, nonflammable hydroxyapatite paper before (d) and during (e) heating in the flame of an alcohol burner, and after heating for 5 minutes (f); (g-i) are photos of the prepared highly flexible, high temperature resistant, nonflammable hydroxyapatite paper before (g) heating in an electric resistance furnace, after heating at 450° C. for 1 hour (h) and when transferred by using a pair of tweezers to another place (i).

See FIG. 4 which shows an optical photo of a highly flexible, high temperature resistant, nonflammable hydroxyapatite paper prepared according to the invention. As shown by FIG. 4, the hydroxyapatite paper prepared is highly flexible, high temperature resistant, nonflammable and has a high level of whiteness according to the invention. See FIG. 5 which demonstrates the flexibility of a highly flexible, high temperature resistant, nonflammable hydroxyapatite paper prepared according to the invention. As shown by FIG. 5, the highly flexible, high temperature resistant, nonflammable hydroxyapatite paper prepared according to the invention can be rolled up randomly, indicating high flexibility. See FIG. 6 which demonstrates the effect of a highly flexible, high temperature resistant, nonflammable hydroxyapatite paper prepared according to the invention in printing words and patterns in color. As shown by FIG. 6, the words and patterns printed in color on the highly flexible, high temperature resistant, nonflammable hydroxyapatite paper prepared according to the invention have a high quality. See FIG. 7 which demonstrates the thermal stability of a common printing paper and a highly flexible, high temperature resistant, nonflammable hydroxyapatite paper prepared according to the invention, wherein (a-c) are optical photos of the common printing paper before (a), during (b) and after (c) heating in the flame of an alcohol burner; (d-f) are optical photos of the highly flexible, high temperature resistant, nonflammable hydroxyapatite paper prepared according to the invention before (d) and during (e) heating in the flame of an alcohol burner, and after heating for 5 minutes (f); (g-i) are optical photos of the highly flexible, high temperature resistant, nonflammable hydroxyapatite paper prepared according to the invention before (g) heating in an electric resistance furnace, after heating at 450° C. for 1 hour (h) and when transferred using a pair of tweezers to another place (i). As shown by FIG. 7, the hydroxyapatite paper prepared according to the invention can endure high temperature and does not burn.

INDUSTRIAL APPLICABILITY

The preparation method of the invention features simple process, low cost, environmental friendliness and adaptability to large-scale production. The hydroxyapatite paper obtained has a high level of whiteness, high flexibility and high temperature resistance, and it does not burn. It can be used for printing words, patterns and images in color with high quality, and for storing important files and archives for a long time. It may also be used in various biomedical areas, pollutant treatment and many other fields.

It is to be understood that various changes or modifications can be made to the invention by those skilled in the art after reading the above teachings of the invention, and these equivalent variations fall in the scope defined by the accompanied claims of the application as well.

What are claimed are as follows:

1. A hydroxyapatite paper comprising an ultralong hydroxyapatite nanowire/microwire having a length of tens to hundreds of micrometers and a diameter of tens to hundreds of nanometers.

2. A method of preparing the hydroxyapatite paper of claim 1, comprising the following step:
dispersing an ultralong hydroxyapatite nanowire/microwire having a length of tens to hundreds of micrometers and a diameter of tens to hundreds of nanometers in a solvent, followed by forming, separation, drying and pressing to obtain the hydroxyapatite paper.

3. The method of claim 2, wherein the solvent is water or an alcohol, wherein the alcohol includes ethanol, methanol, propanol, isopropanol and butanol.

4. The method of claim 2, wherein the method further comprises adding additives to the solvent, wherein the additives include inorganic additives and organic additives, wherein the inorganic additives include sodium silicate, potassium silicate, sodium borate and potassium borate; and the organic additives include polylactic acid, polyethylene glycol, polyvinyl alcohol, polystyrene and polyurethane.

5. The method of claim 2, wherein the separation includes filtration and vacuum filtration, and the temperature for drying is 20-200° C.

* * * * *